(12) United States Patent
Goroszeniuk

(10) Patent No.: US 7,970,479 B2
(45) Date of Patent: Jun. 28, 2011

(54) PERIPHERAL NEUROSTIMULATION

(76) Inventor: Teodor Goroszeniuk, London (GB)

( * ) Notice: Subject to any disclaimer, the term of this patent is extended or adjusted under 35 U.S.C. 154(b) by 422 days.

(21) Appl. No.: 10/968,058

(22) Filed: Oct. 20, 2004

(65) Prior Publication Data
US 2005/0085870 A1   Apr. 21, 2005

(30) Foreign Application Priority Data

Oct. 20, 2003 (GB) .................................. 0324468.8
May 7, 2004 (GB) .................................. 0410171.3

(51) Int. Cl.
*A61N 1/05* (2006.01)
(52) U.S. Cl. ......... 607/116; 607/115; 607/117; 607/118
(58) Field of Classification Search ........... 607/115–118
See application file for complete search history.

(56) References Cited

U.S. PATENT DOCUMENTS

| 6,233,488 | B1 * | 5/2001 | Hess ............................... 607/58 |
| 2001/0001125 | A1 * | 5/2001 | Schulman et al. ................ 607/2 |
| 2002/0055761 | A1 * | 5/2002 | Mann et al. ...................... 607/41 |
| 2003/0078643 | A1 * | 4/2003 | Schulman et al. ............. 607/116 |
| 2004/0015202 | A1 * | 1/2004 | Chandler et al. ................ 607/46 |

* cited by examiner

*Primary Examiner* — Niketa I Patel
*Assistant Examiner* — Rex Holmes
(74) *Attorney, Agent, or Firm* — Dennison, Schultz & MacDonald

(57) ABSTRACT

A percutaneous stimulating device 10 comprises a self-contained permanent or long-term unit for neuromodulation in the management of chronic pain and for cosmetic applications in accordance with the invention. It comprises a stimulating zone 12 with one or more electrodes 14, and an integral control unit 16 electrically connected by means of suitable wires 18 to the stimulating zone. The control unit 16 is arranged to supply an electrical stimulating signal to the electrode(s) 14.

The device is in the form of a closed cylinder having a diameter of 1.2 to 1.5 mm and is no more than 70 mm in length so that it can be located and inserted into a patient using a stimulating needle, which is subsequently withdrawn from the patient when the device is in place.

The invention extends to a method for long term pain management by means of neuromodulation using the percutaneous device in accordance with the invention to supply a stimulating signal at between 2 and 50 Hz.

12 Claims, 3 Drawing Sheets

PERIPHERAL NEUROSTIMULATION

BACKGROUND OF THE INVENTION

This invention relates to devices for peripheral neurostimulation for the long term management of chronic pain and for cosmetic applications, and in particular to such percutaneous devices. It also relates to a method for performing such neurostimulation.

Neuromodulation has been established in medical practise since the introduction of peripheral nerve stimulation in 1965 and spinal cord stimulation in 1967. At present some 50 000 units are now implanted in patients around the world (2002). The majority of the implants are carried out for spinal cord stimulation, and similar applications like retrograde, sacral roots or nerve stimulation. Implantable percutaneous devices usually have several discrete elements: an electrode, connections or an extension and a power source. The power to an electrode can be supplied from an external battery by means of a radio frequency (RF) receiver or from internally implanted IPG battery unit.

The use of peripheral neuromodulation technique is expected to expand during this decade. However, the available existing systems are less than satisfactory as they are too large and they comprise several separate components, and generally require a surgical procedure to introduce them.

SUMMARY OF THE INVENTION

In accordance with the invention, a percutaneous stimulating device for long-term peripheral neuromodulation in pain management and cosmetic applications comprises a stimulating zone with one or more electrodes, and a control unit electrically connected to the electrode(s) and capable of supplying an electrical stimulating signal to the electrode(s), the device being formed of an inert material and hermetically sealed and of a substantially cylindrical form so dimensioned as to be suitable for insertion into a patient through a stimulating needle.

The device thus comprises an electrode which is combined with or arranged to be connected to a power source or receiver, to permit its introduction via a stimulating needle which is used both to assist its proper location and insertion in order to provide the required neurostimulation to the patient.

In use, the proper location for the device is determined by inserting a stimulating needle and detecting the response to a stimulating signal. The device is then inserted percutaneously through the stimulating needle or cannula. Where the power source or control unit is too wide to pass through the stimulating needle or cannula, the latter can be peeled away to allow the wider part of the device to be gently pushed under the patient's skin or inserted by making a small incision.

The percutaneous introduction of such a permanent device for peripheral neuromodulation by means of a stimulating needle will considerably simplify the procedures on patients and will allow them to be carried out by other than by invasive surgery. It will also minimise any surgical trauma during the insertion of this type of unit.

The device is thus intended to remain in place permanently, or at least many weeks or months which is made possible either by the use of lithium or other suitable long-life batteries which are also introduced percutaneously, or by means of a radio frequency (RF) signal to a transformer connected to the control unit which converts the signal to the required amplitude and frequency for the electrode(s). It is also possible to apply the RF output from the transformer directly to the electrode(s) or to store the energy in a capacitor.

The diameter of the device will not be greater than 2 mm and preferably 1.5 mm, and ideally less than 1.2 mm to permit its insertion by means of a stimulating needle. It will be less than 70 mm long so that it can be inserted through a stimulating needle or catheter, and preferably less than 40 mm, though for cosmetic applications shorter versions of less than 20 mm or even as short as 6 mm may be required. As electronic components become smaller even smaller versions may become feasible, and the cost of the device is likely to decrease significantly.

The preferred stimulation frequency range of the device is between 1 and 50 Hz and optimally between 2 and 10 Hz. This low frequency has an unexpectedly successful effect on the treatment of chronic pain. A current of between 0.15 and 15 mA and preferably between 2 and 10 mA is found to be very successful. This may be produced by applying a voltage of between 2 and 10 volts to the electrodes.

Although it is preferred that the power supply for the control unit is an integral part of it, until the electronics has been made small (or inexpensive) enough it may connected to the stimulating part of the device after insertion. In practice this may require a small incision adjacent to the point where the stimulating needle is inserted in order to bury the power supply unit.

In an increasing proportion of cases at present, an external power source would be provided; in response to the patient's requirements, the RF signal is transmitted to the device to provide the desired level of neurostimulation.

The device is advantageously be provided with small flexible wings close to the electrode(s), which in use act to hold the device in position.

As the device may fail, or otherwise need to be removed, in one embodiment, it is provided with a drawstring at the end opposite to the stimulating zone to enable it to be removed from a patient after insertion without the need for a surgical procedure, although a small incision may be necessary.

The device is intended in practice to be supplied already inside a stimulating needle assembly ready for percutaneous insertion into a patient. This specifically increases the precision in inserting and positioning the electrodes to treat the pain and avoids the need for a surgical procedure, although in some instances a small incision may subsequently be required to insert the control unit or power supply, if separate.

The diameter of the device can be as small as permitted by the technology; today, a percutaneous device having a diameter of less than 1.5 mm and a length of from 6 mm to 70 mm long is feasible using the very most sophisticated electronics, but it is expected that within a few years technology will allow the device to be produced significantly less expensively providing access to many more people who are known to suffer from chronic pain. Although the exterior of the device is made of an inert material, in the case of the longer units they may be slightly flexible. In the case of the smallest devices, it may be necessary to use a wire or other tool to make sure that they are expelled correctly at the end of the stimulating needle during insertion.

The advantage of percutaneous devices in accordance with the invention is that they are small enough to be inserted and located by means of a stimulating needle, and small enough to remain in place adjacent to the nerve to be stimulated (or at a suitable other position which will remotely stimulate the desired site) for many months or even years as required.

BRIEF DESCRIPTION OF THE DRAWINGS

The invention will now be described specifically by way of example with reference to the accompanying drawings, in which.

DETAILED DESCRIPTION OF THE INVENTION

Figure 1:
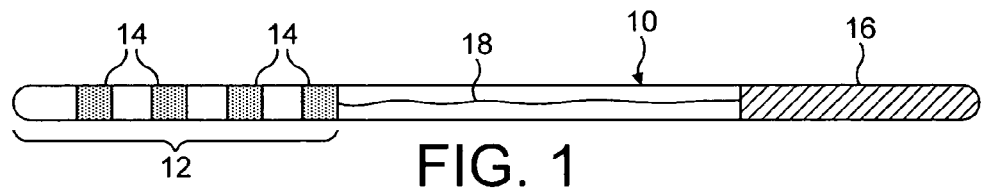
FIG. 1 is a diagrammatic view of a fully self-contained percutaneous stimulating device.
Figure 1A:
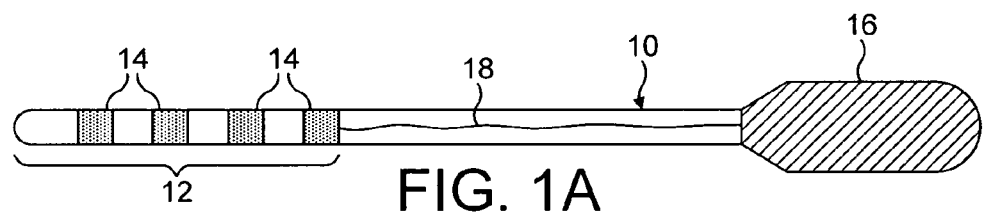
FIG. 1A is a diagrammatic view of an alternative version of a percutaneous stimulating device having an enlarged portion to accommodate its power supply and control unit.

FIG. 1 and 1A show diagrammatically two embodiments of a device 10 which is a self-contained permanent or long-term unit for neuromodulation in the management of chronic pain and for cosmetic applications in accordance with the invention. It comprises a stimulating zone 12 provided with one or more electrodes 14, and an integral control unit 16 electrically connected by means of suitable wires 18 to the stimulating zone 12. The control unit 16, which incorporates a self-contained power source, is capable of supplying an electrical stimulating signal to the electrode(s) 14.

The body of the device in FIG. 1 has a generally cylindrical form with a diameter of 1.2 to 1.5 mm. It is between 20 and 70 mm in length so that it can be inserted into a patient using a semi-rigid stimulating needle (similar to that shown in FIG. 3).

In use the stimulating needle is used to identify the most effective position for the device. The needle is inserted close to the muscle or nerve in question while a stimulating signal is applied to it. The response to the signal is measured until it shows the optimum position for the device. The device is expelled from the stimulating needle which is then carefully withdrawn from the patient leaving the device properly located in the desired position.

It is anticipated that as electronic components decrease in size it will be possible to manufacture the device in ever shorter lengths, viz. shorter than 20 mm or even less than 10 mm. Very small devices which may be no longer than 6 mm lend themselves particularly to cosmetic treatments, and to facial implants. Longer devices may be used for areas where a larger area of treatment is required, such as wrists, shoulder or the back.

The outer casing is inert to body fluids and may be of metal or a plastics material. The longer devices are semi-rigid or slightly flexible to allow slight movement in the patient.

The control unit allows the stimulation frequency range of the device to be set between 1 and 50 Hz; in most cases however it has been found to be most effective between 2 and 10 Hz. It is arranged to deliver a current to the electrodes, which can be set in the range of 0.15 mA to 15 mA, though in practice a stimulating current of between 2 and 12 mA is found to be most effective.

Both the amplitude and the frequency are adjustable and are adjusted to achieve the most beneficial effect on the source of pain in the patient. All of the devices described are adapted to operate at this preferred frequency range.

The device 10 shown in FIG. 1A is similar to that in FIG. 1, but has an enlarged control unit 16 to accommodate a longer-lasting power source or battery. Whilst the body this device is intended to be located and inserted into a patient as described above, it may require a small incision to enable the end containing the control unit 16 to be satisfactorily implanted. In this case the control unit 16 may be inserted using a peel-away catheter which can be peeled off to allow it to be inserted under the skin by making a small incision.

Alternatively, the percutaneous devices 10 shown in FIGS. 1 and 1A may have a control unit 16 comprising a radio frequency (RF) receptor. The RF receptor is arranged to receive a signal and its energy from an external unit, not shown, to generate the signal in terms of its frequency and amplitude. Thus the signal from the control unit 16 may be adjusted or controlled by the patient or a practitioner by means of controls on the external unit as required. The external unit will conveniently be carried by or strapped to the patient to facilitate prolonged treatment, although a five-minute session one to three times a day will generally provide satisfactory relief.

The advantage of using an RF receptor is that the device can be controlled externally and the power to the device can be supplied by means of the RF signal thus avoiding the need for the device to be fitted with a battery which ultimately needs to be replaced or recharged.

Figure 2:
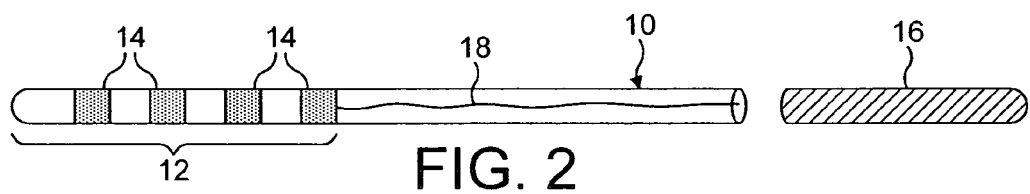
FIGS. 2 and 2A are a diagrammatic views of alternative forms of the devices in FIG. 1 and 1A whereby the control unit can be removed from the main body of the device to facilitate insertion of the device into a patient, and subsequently reconnected.
Figure 2A:
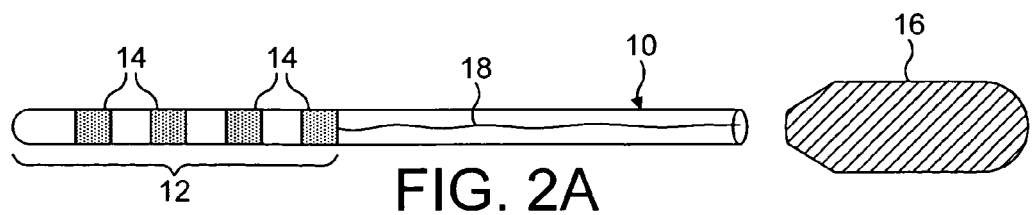

The percutaneous devices 10 shown in FIGS. 2 and 2A are similar to those in FIGS. 1 and 1A, but the control unit 16 is supplied separately from the main body of the device 10. The body of the device can be inserted and located using a stimulating needle. The control unit 16 is then attached or plugged in at 19 once the device is substantially in place. As the control unit is the most bulky part of the device, this embodiment has the advantage that the control unit only needs to be attached to the main body of the device once the stimulating needle has been withdrawn. In the embodiment shown the control unit/power supply is hermetically joined to the main body of the device after location of the electrodes. In another embodiment, not shown, the control unit/power supply is connected by flexible wires which allows it to be implanted at a convenient location. As mentioned above, a small surgical incision may be required for the control unit.

The percutaneous devices 10 shown in FIGS. 2 and 2A may also be equipped with an RF receptor or transformer in the control unit 16 as described in relation to FIGS. 1 and 1A.

Figure 3:
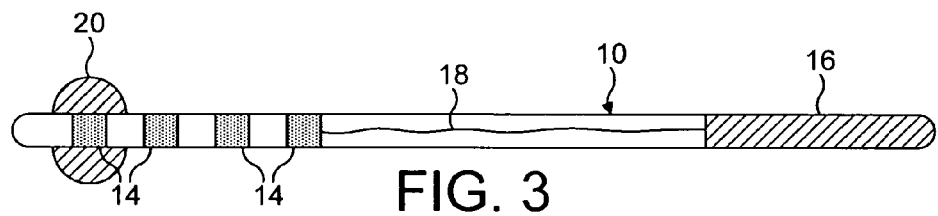
FIG. 3 is a diagrammatic view a device as shown above, provided with stabilising wings.

FIG. 3 shows a percutaneous device 10 which may be similar to any of those shown in the Figures above, but it is provided with soft, flexible plastic wings 20 in or adjacent to the stimulating zone 12, which wings once the device is inserted into a patient act to maintain it more securely and accurately in place in the patient.

Figure 3A:
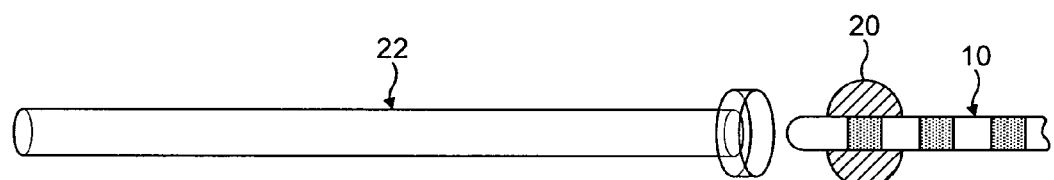
FIGS. 3A to C illustrate the use of a stimulating needle to introduce the device shown in FIG. 3 into a patient.
Figure 3B:
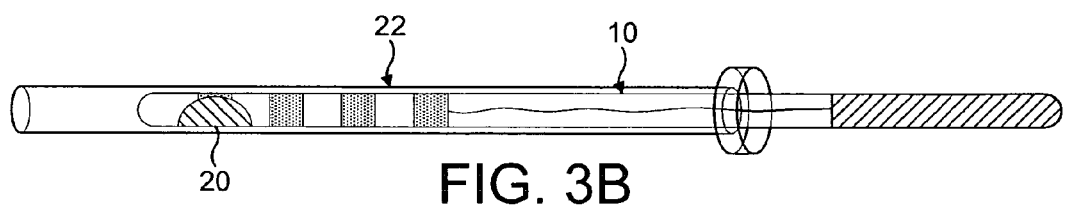
Figure 3C:
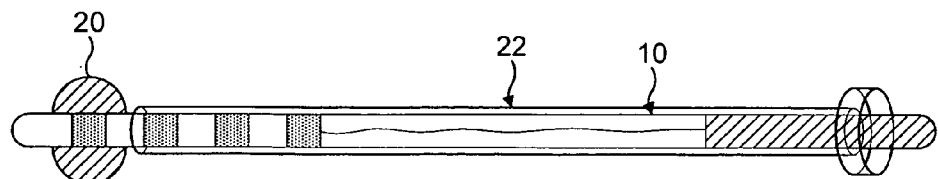

FIGS. 3A to C illustrate diagrammatically the insertion of the percutaneous device in FIG. 3 into a patient using a stimulating needle 22. In FIG. 3A the device is introduced into the stimulating needle 22. In FIG. 3B the stimulating needle is ready for insertion into the patient. In FIG. 3C the percutaneous device is in place in the patient, and the stimulating needle is ready to be withdrawn. When it is removed from the patient it leaves the stimulating device in place. It may be necessary to use a wire or tool to expel the stimulating device from the needle, particularly in the case of very short devices as used for facial implants. Ideally, the device is supplied positioned within the stimulating needle ready for use.

Figure 4:
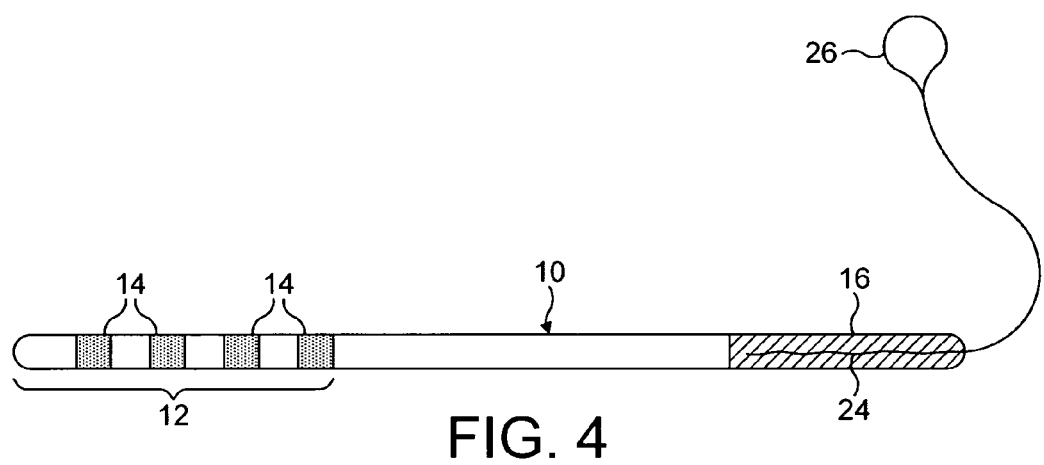
FIG. 4 shows a device with a draw string to enable it to be removed from a patient.

FIG. 4 shows how the percutaneous device can also incorporate a safety net 24 at the outer end of the device, attached to a drawstring with a ring-pull 26, to enable it to be removed subsequently from an implantation site without the need for a full surgical intervention.

The advantage of a percutaneous device in accordance with the invention is that it is self-contained and small enough to be inserted and located by means of a stimulating needle. The introduction of such a permanent stimulating device for peripheral neuromodulation by means of a stimulating needle considerably simplifies the procedures on patients and allows it to be carried out other than by surgery. It also reduces any surgical trauma during the insertion of this type of percutaneous device. Additionally it is small enough to remain in place adjacent to the nerve to be stimulated (or at a suitable other position which will remotely stimulate the desired site) and be effective for many months or even years as required and without significant inconvenience to the patient.

In all cases the percutaneous device is placed in its desired position using the stimulating needle. A specialist doctor determines the area of implantation and the ranges of the stimulating frequency and current. Where there is an RF connection between the device and an external unit the patient has a greater choice of use of the device to provide relief. He will also be able to vary the frequency and current within the parameters preset by the specialist practitioner to obtain optimum relief.

What is claimed is:

1. A method for long-term pain management and for cosmetic applications by means of percutaneous peripheral neuromodulation, comprising:

inserting into a patient a single and hollow stimulating needle in a zone to be stimulated;

locating an optimum position of the zone to be stimulated by applying a stimulating signal to the stimulating needle and optimizing a response from a muscle or a nerve, inserting percutaneously into the patient through the single and hollow stimulating needle, at the optimum position, a main body of an integral neurostimulation device, the main body comprising an elongated, tubular hollow container closed at a distal end thereof, and having disposed therein at least one electrode for creating a stimulating zone for the device, and means for electrically attaching the at least one electrode to an electronic control unit, removing the single and hollow stimulating needle from the inserted stimulating portion, and physically attaching the inserted main body at a proximal end thereof directly to an integral electronic control unit with electrical attachment of the at least one electrode thereto, to form the integral neurostimulation device as a hermetically sealed, substantially cylindrical unit of a length no more than 70 mm, the control unit comprising a body having disposed therein means for supplying an electrical stimulating signal to at the least one electrode, the means for supplying comprising at least one of a battery and a radio frequency receiver within the hermetically sealed unit, with electrical connection of the means for supplying.

2. A method as claimed in claim 1, wherein the control unit is inserted by means of a surgical incision.

3. A method as claimed in claim 1, wherein the stimulating signal is at a stimulation frequency in a range between 1 and 50 Hz.

4. A method as claimed in claim 1, wherein the stimulation frequency is in a range between 2 and 10 Hz.

5. A method as claimed in claim 1, wherein the stimulating signal is supplied to the patient in a current range between 0.15 and 10 mA.

6. A method as claimed in claim 5, wherein the current range is between 2 and 10 mA.

7. A method as claimed in claim 1, wherein the device supplies a stimulating signal at a voltage in a range between 2 and 10 volts.

8. A method as claimed in claim 1, wherein the length is no more than 40 mm.

9. A method as claimed in claim 8, wherein the length is no more than 20 mm.

10. A method as claimed in claim 1, wherein the hermetically sealed, substantially cylindrical unit has a diameter of no more than 2 mm.

11. A method as claimed in claim 10, wherein the diameter is no more than 1.5 mm.

12. A method as claimed in claim 11, wherein the diameter is less than 1.2 mm.

* * * * *